United States Patent [19]

Bonin

[11] Patent Number: 5,418,255
[45] Date of Patent: May 23, 1995

[54] METHOD OF TREATING ALCOHOL DEPENDENCE

[75] Inventor: Wilfred P. Bonin, Houston, Tex.

[73] Assignee: Bonin Centers, Inc., Houston, Tex.

[21] Appl. No.: 4,200

[22] Filed: Jan. 13, 1993

Related U.S. Application Data

[63] Continuation of Ser. No. 717,859, Jun. 19, 1991, abandoned, which is a continuation of Ser. No. 455,496, Dec. 22, 1989, abandoned.

[51] Int. Cl.⁶ ............................................. A61K 31/045
[52] U.S. Cl. .................................... 514/724; 514/811
[58] Field of Search ................................ 514/724, 811

[56] References Cited

PUBLICATIONS

Chem Abstracts 99(15):117679p Gaspar Oct. 11, 1982.
Remington's Pharmaceutical Sciences 15th ed 1975 pp. 1289-1290.

*Primary Examiner*—Raymond J. Henley, III
*Attorney, Agent, or Firm*—Conley, Rose & Tayon

[57] ABSTRACT

Disclosed is a method of treating alcohol dependence in which an ethanol solution is intravenously administered. The ethanol concentration is preferably about 5 to 25% by volume, and more preferably about 10 to 20% by volume. The solution is administered over several days in progressively decreasing quantities. For those treated for the first time, it is preferred that the treatment program extend over ten days. Patients previously treated who re-lapse into drinking can usually be effectively re-treated with a program lasting for a shorter period, such as for six days.

13 Claims, No Drawings

METHOD OF TREATING ALCOHOL DEPENDENCE

This application is a Continuation of prior U.S. application Ser. No. 07/717,859, Filing Date Jun. 19, 1991, now abandoned, and which is a continuation of application Ser. No. 07/455,469, Filing Date Dec. 22, 1989, now abandoned.

FIELD OF THE INVENTION

The invention relates to a treatment for alcohol dependence involving intravenous infusion of an alcohol solution.

BACKGROUND OF THE INVENTION

Alcohol dependence (also known as alcoholism) is well recognized as substance abuse disorder. See Diagnostic and Statistical Manual of Mental Disorders 3rd. Ed. (1980), American Psychiatric Association, Washington D.C., ("DSM III") at p. 169. Alcohol dependence is more common among family members than in the general population, indicating that there is a genetic factor involved in this disease. DSM III at p. 169.

Alcohol dependence can be diagnosed where there is either tolerance to increased amounts of alcohol, or withdrawal symptoms when drinking is ceased or reduced. It can also be diagnosed where there is a pattern of pathological alcohol use, or impairment in social or occupational functioning due to alcohol use. The latter diagnostic criteria involve the behavior which often causes serious problems for both the alcoholic and those close to him or her. Such behavior includes violence while intoxicated, absence from work, loss of employment, legal problems related to alcohol—e.g., arrests for intoxicated behavior or traffic accidents while intoxicated—and arguments or difficulties with family or friends because of excessive alcohol use. DSM III at p. 170.

It is estimated that there are several million people suffering from alcohol dependence in United States alone. Of this group, only a small percentage will ever seek treatment. Conventional treatment programs include some or all of the following procedures: counselling; group sessions which engender support for the alcohol dependent individuals; administration of sedatives, tranquilizers or barbiturates to counter withdrawal symptoms; administration of substances which cause a temporary intolerance to ingestion of alcohol.

Experience has shown that the conventional treatment methods are effective in only a small percentage of cases. Typically, only about 3 to 10% of entering patients will succeed if they follow a conventional treatment program. This low success rate probably leads the majority of alcoholics to perceive their situation as hopeless, and avoid seeking treatment. These same persons, however, could be encouraged to seek treatment if they perceived there was a better chance of success. Thus, a multitude—made up of those for whom conventional treatments fail as well as those not currently seeking treatment because of the low success rate—would be well served by a more effective treatment for alcoholism than is currently available.

SUMMARY OF THE INVENTION

The invention is a method of treating alcohol dependence in which an ethanol solution is infused intravenously into a patient. Typically, for the new patient, the treatment is continued for ten days, with a steady decrease in the amount of ethanol infused each day. It is preferred that about 40 to 50 ml of ethanol (in a greater total volume of solution) be initially administered in two separate aliquots, and that the volume of ethanol be decreased by about 2 to 4 ml per day for the first three days. On the fourth day, the volume of ethanol is decreased by about 20 ml, and this volume is given in only one aliquot. From the fourth through the tenth day, the volume is again decreased by about 2 ml per day so that on the final day, preferably only about 4 ml of ethanol is infused in one aliquot.

The preferred concentration of ethanol in solution is about 10 to 20% by volume. However, the concentration and the total volume of solution infused can vary considerably, depending primarily on the tolerance and weight of the patient.

It has been found that after the initial treatment program, the patients who suffer recidivism can often be effectively retreated by a six day course of alcohol infusion, rather than the full ten day treatment program. With this shorter program, the same volume of ethanol, i.e. about 40 to 50 ml, is initially administered, and it is then decreased following the same schedule described above for the ten day treatment. On the final day of treatment, preferably about 12 ml of ethanol is infused.

The invention will now be described in further detail with reference to following examples and results.

DESCRIPTION OF THE PREFERRED EMBODIMENTS

To carry out the invention, an ethanol solution, preferably 10–20% by volume, is intravenously infused to the alcohol dependent individual. The concentration of alcohol in solution can vary from about 5% by volume to about 25% by volume. Ethanol concentrations of substantially less than 5% have been found less effective in treatment, and concentrations in excess of 25% can cause discomfort at the administration site. One suitable alcohol solution for infusion which is available in prepackaged form is manufactured by Kendall-McGaw Laboratories, Inc., and contains 5% dextrose and 10% ethanol in distilled water. This solution is intended for nutrition, and therefore includes dextrose. Although there is actually no need for dextrose when treating alcohol dependence, its presence does not create any complications or adverse effects.

The infusion procedure is performed according to standard techniques and procedures. In brief, an infusion bag or bottle containing the solution is hung from a support. A drip connector is attached to the bottle, and tubing is attached to the drip connector. Air is then expelled from the tubing, and after clamping the tubing, a needle is attached to the tubing. The vein is then punctured with the needle, and the needle is immobilized against the arm. The drip connector allows adjustment of the infusion rate.

A typical administration program, using the 5% dextrose and 10% ethanol solution, would begin with infusion of 220 ml of solution twice daily on the first day. At least about two and one-half hours rest or waiting period should be given between successive infusions.

For most patients, one would not want to infuse more than 220 ml in one hour. This is because the metabolism rate of ethanol is usually not more than 20 ml per hour, and if 220 ml of the aforementioned 10% ethanol solution is infused in one hour, then slightly more alcohol is being infused than can be metabolized. However, the rate of infusion can vary greatly, and can exceed these limits, depending on the weight of the patient and especially on his tolerance for alcohol. Tolerance is usually related to the severity of alcohol dependence.

It is recommended that the alcohol be infused more slowly than 220 ml per hour at the beginning of the infusion. The rate can be gradually increased if the patient appears tolerant. The patient should be monitored throughout the infusion for adverse reactions. If these appear, the infusion rate should be decreased.

Following the above-described treatment on the first day, the preferred treatment schedule, using the aforementioned 10% ethanol solution, is as follows:

Day two: 200 ml, twice daily;
Day three: 180 ml, twice daily;
Day four: 160 ml, once daily;
Day five: 140 ml, once daily;
Day six: 120 ml, once daily;
Day seven: 100 ml, once daily;
Day eight: 80 ml, once daily;
Day nine: 60 ml, once daily;
Day ten: 40 ml, once daily.

Again, for the second and third days on which two infusions are given, at least two and one-half hours should remain between successive infusions. The recommended infusion rate can be determined using the guidelines and considerations mentioned above. In general, not more than 20 ml of alcohol should be infused per hour. However, the infusion rate can exceed this limit depending on patient's weight and tolerance.

As noted above, solutions with different concentrations of alcohol, i.e. from about 5 to 25% can be used in treatment. When the concentration is varied, the treatment schedule, and the guidelines for calculating the infusion rate do not change. The volume of solution is adjusted so that the same volume of alcohol as set forth above is infused with each treatment. For example, if using a 20% ethanol solution, one-half the solution volume set forth above would be infused each time. Thus, 110 ml of the 20% solution would be infused twice on the first day, 100 ml would be infused twice on the second day, and so on through the tenth day, at which time 20 ml would be infused once.

Although an initial ten day treatment program is preferred and has been found effective in most patients, a shorter or longer program can also be used. In fact, for those with severe alcohol dependence, a longer treatment program, e.g., up to twenty days, is recommended. Further, a greater or lesser quantity of alcohol than listed above can be infused, and a greater or lesser number of treatments can be administered each day.

Recidivists can often be effectively re-treated. The re-treatment program is generally of shorter duration, and preferably lasts for six days. With the shorter treatment, the initial quantity of alcohol infused is preferably the same as with the ten day treatment, i.e., on the first day preferably about 40 to 50 ml of ethanol is administered. Preferably, if using the preferred 10% ethanol solution, 22 ml is administered twice on the first day. The amount of solution infused is then reduced as follows:

Day two: 200 ml, twice daily;
Day three: 180 ml, twice daily;
Day four: 160 ml, once daily;
Day five: 140 ml, once daily;
Day six: 120 ml, once daily.

If the shorter treatment program is not effective, a longer re-treatment program can be used. Further, the volume of solution, the rate of infusion, and the concentration can all be varied with the shorter program in the same manner, and subject to the same considerations, in which they are varied in the longer ten day program.

The treatment program described above has been used experimentally by the inventor for some time. In fact, 1540 patients have been treated to date using this program. Patients treated before about 1985 received a 20% ethanol solution, in the manner described above. Most patients treated since about 1985 received the 10% ethanol solution manufactured by Kendall-McGaw, in the manner described above. Recently, 487 of the total number of patients treated were contacted to monitor their progress. The results from these patients are shown below in Table I.

TABLE I

| For Patients Treated Between: | Total Patients Treated | Number of Patients Contacted | Number of Patients Abstinent | % of Total Which Were Abstinent |
|---|---|---|---|---|
| 1940–1950 | 182 | 11 | 4 | 36.4% |
| 1950–1960 | 420 | 30 | 11 | 36.7% |
| 1960–1970 | 485 | 108 | 40 | 37.0% |
| 1970–1980 | 307 | 218 | 78 | 35.8% |
| 1980–1989 | 146 | 120 | 55 | 45.8% |
| Totals: | 1540 | 487 | 188 | 38.6% |

| For Patients Treated Between: | Recidivist Patients Re-treated | Patients Abstinent After Re-treatment | % of Patients Re-treated Which Were Abstinent |
|---|---|---|---|
| 1940–1950 | 1 | 1 | 100% |
| 1950–1960 | 4 | 2 | 50% |
| 1960–1970 | 7 | 2 | 28.6% |
| 1970–1980 | 23 | 9 | 39.0% |
| 1980–1989 | 15 | 8 | 53.3% |
| Totals: | 50 | 22 | 44% |

It can be seen that of the patients contacted, 38.6% remained abstinent. This figure is considerably better than the 3 to 10% cure rate associated with conventional treatment methods. Moreover, it is even more encouraging to note that of the recidivist patients which were re-treated, 44% have remained abstinent. This indicates that re-treatment is a valuable adjunct therapy for recidivism.

A proposed explanation for the effectiveness of this treatment is that alcohol addiction is the result of an immune response to the ethanol antigen. The intestine is lined by a great number of macrophage. Phagocytization of an antigen by macrophage is usually the first step in the immune response. Thus, when alcohol is introduced intravenously, it does not pass through the macrophage-rich intestine, and the immune response is substantially ameliorated. At the same time, however, this alcohol is available in the blood stream to satisfy the needs of the central nervous system and abate the usual withdrawal symptoms. Because the amount of alcohol administered is gradually decreased, the patient is desensitized to the alcohol antigen which caused the allergic-type reactions. Ultimately, the patient becomes immunologically non-reactive to alcohol, and the craving for it diminishes.

It should be understood that the foregoing terms, expressions and examples are exemplary only and not limiting, and that the scope of protection is defined only by the claims which follow and includes all equivalents of the subject matter of the claims.

What is claimed is:

1. A method of treating alcohol dependence in an individual, said method comprising mitigating the individual's craving for alcohol by intravenously administering an effective alcohol dependence treating amount of an ethanol solution to the individual on a daily basis for about 6 to about 30 days, wherein a progressively decreasing amount of ethanol is administered during the treatment period such that the interval between successive doses of alcohol is not more than 48 hours.

2. The method of claim 1 wherein the ethanol concentration is about 5 to 25% by volume.

3. The method of claim 2 wherein the ethanol concentration is about 10 to 20% by volume.

4. The method of claim 1 wherein the solution is administered for about six to about ten days.

5. The method of claim 4 wherein a progressively decreasing volume of solution is administered on each successive day.

6. The method of claim 5 wherein the solution is administered for no more than ten successive days.

7. The method of claim 6 wherein the ethanol concentration in the solution is about 10 to 20% by volume.

8. The method of claim 7 wherein sufficient solution is infused so that 40 to 50 ml of ethanol is administered on the first day, and the quantity of solution infused is progressively decreased.

9. The method of claim 4 wherein sufficient solution is infused so that 40 to 50 ml of ethanol is administered on the first day, and the quantity of solution infused is progressively decreased over the next five days.

10. A method of treating alcohol dependence comprising intravenously administering to an alcohol dependent individual the following quantities of a 10% by volume ethanol solution over a period of ten days:
   220 ml, twice daily on the first day;
   200 ml, twice daily on the second day;
   180 ml, twice daily on the third day;
   160 ml, once daily on the fourth day;
   140 ml, once daily on the fifth day;
   120 ml, once daily on the sixth day;
   100 ml, once daily on the seventh day;
   80 ml, once daily on the eighth day;
   60 ml, once daily on the ninth day;
   40 ml, once daily on the tenth day.

11. The method of claim 10 wherein on the first, second and third days, at least a two and one-half hour interval is left between the two daily infusions.

12. A method of treating alcohol dependence in a recidivist already treated at least once by intravenously infusing an ethanol solution comprising intravenously administering the following quantities of a 10% by volume ethanol solution over a period of six days:
   220 ml, twice daily on the first day;
   200 ml, twice daily on the second day;
   180 ml, twice daily on the third day;
   160 ml, once daily on the fourth day;
   140 ml, once daily on the fifth day;
   120 ml, once daily on the sixth day.

13. The method of claim 12 wherein on the first, second and third days, an interval of at least two and one-half hours is left between the two daily infusions.

* * * * *